United States Patent
Wong et al.

(10) Patent No.: US 9,289,428 B2
(45) Date of Patent: Mar. 22, 2016

(54) CONVENIENTLY INJECTABLE OR IMPLANTABLE SUSTAINED-RELEASE ANTIOXIDANT FORMULATIONS FOR THERAPIES OF OCULAR MALADIES OR CANCER

(75) Inventors: Vernon G. Wong, Menlo Park, CA (US); Louis L. Wood, Potomac, MD (US); Carol Wood, legal representative, Potomac, MD (US)

(73) Assignee: RAMSCOR, INC., Menlo Park, CA (US)

( * ) Notice: Subject to any disclaimer, the term of this patent is extended or adjusted under 35 U.S.C. 154(b) by 0 days.

(21) Appl. No.: 14/124,592

(22) PCT Filed: Jun. 11, 2012

(86) PCT No.: PCT/US2012/041927
§ 371 (c)(1),
(2), (4) Date: Jan. 16, 2014

(87) PCT Pub. No.: WO2013/058838
PCT Pub. Date: Apr. 25, 2013

(65) Prior Publication Data
US 2014/0329785 A1    Nov. 6, 2014

Related U.S. Application Data

(60) Provisional application No. 61/495,737, filed on Jun. 10, 2011.

(51) Int. Cl.
| | |
|---|---|
| A61K 31/5377 | (2006.01) |
| A61K 31/573 | (2006.01) |
| A61K 45/06 | (2006.01) |
| A61K 31/355 | (2006.01) |
| A61K 31/122 | (2006.01) |
| A61K 31/4045 | (2006.01) |
| A61K 31/375 | (2006.01) |
| A61K 31/05 | (2006.01) |
| A61K 9/00 | (2006.01) |

(52) U.S. Cl.
CPC ............ *A61K 31/5377* (2013.01); *A61K 9/0019* (2013.01); *A61K 9/0024* (2013.01); *A61K 9/0048* (2013.01); *A61K 9/0051* (2013.01); *A61K 31/05* (2013.01); *A61K 31/122* (2013.01); *A61K 31/355* (2013.01); *A61K 31/375* (2013.01); *A61K 31/4045* (2013.01); *A61K 31/573* (2013.01); *A61K 45/06* (2013.01)

(58) Field of Classification Search
CPC ............ A61K 31/375; A61K 31/4045; A61K 9/0024; A61K 31/5377; A61K 45/06; A61K 31/05; A61K 2300/00; A61K 31/355; A61K 31/573; A61K 31/122; A61K 9/0019; A61K 9/0051; A61K 9/0048
See application file for complete search history.

(56) References Cited

U.S. PATENT DOCUMENTS

| 8,425,929 B2 * | 4/2013 | Huang et al. ................. 424/428 |
| 2007/0207116 A1 | 9/2007 | Brown |
| 2008/0038316 A1 | 2/2008 | Wong et al. |
| 2011/0111006 A1 | 5/2011 | Wong et al. |

FOREIGN PATENT DOCUMENTS

WO    2007/103960 A1    9/2007

OTHER PUBLICATIONS

Astaxanthin Safety Data Sheet, Cayman Chemical 2010 (revised 2012), p. 1-4.*
Miki, W., "Biological functions and activities of animal carotenoids." Pure and Applied Chemistry 63.1 (1991): 141-146.*
The Extended European Search Report, mailed Oct. 20, 2014, cited in related European Patent Application No. 12841354.9, filed Jun. 11, 2012.
Ding, S., "Recent developments in ophthalmic drug delivery," Pharmaceutical Science & Technology Today, 1998, vol. 1, No. 8, pp. 328-335.
Orosz, K.E. et al., "Delivery of antiangiogenic and antioxidant drugs of ophthalmic interest through a nanoporous inorganic filter," Molecular Vision, 2004, vol. 10, pp. 555-565.
Rose, R. C. et al., "Ocular oxidants and antioxidant protection," Experimental Biology and Medicine, 1998, vol. 217, pp. 397-407.

* cited by examiner

*Primary Examiner* — Samantha Shterengarts
*Assistant Examiner* — Matt Mauro
(74) *Attorney, Agent, or Firm* — Wiley Rein LLP

(57) ABSTRACT

The present embodiments provide for sustained release formulations of antioxidants that are useful in treating afflictions of the eye and tumors.

6 Claims, 5 Drawing Sheets

CONVENIENTLY INJECTABLE OR IMPLANTABLE SUSTAINED-RELEASE ANTIOXIDANT FORMULATIONS FOR THERAPIES OF OCULAR MALADIES OR CANCER

RELATED APPLICATIONS

The present application is a 371 application of International Patent Application No. PCT/US2012/041927, filed Jun. 11, 2012, which claims priority benefit of U.S. Patent Application No. 61/495,737, filed Jun. 10, 2011, and are fully incorporated herein.

FIELD OF THE INVENTION

The present invention provides for novel liquid and solid, sustained release formulations of antioxidants for intraocular and intratumoral injection or implantation as novel methods of treatment of ocular afflictions and tumors/cancer.

BACKGROUND

In Earth's oxygen rich environment, life forms have evolved that utilize the energy rich chemistries of oxygen to efficiently operate their life processes. But, in doing so they must constantly protect themselves from unwanted damaging free-radical oxidative reactions. These reactive oxygen species include superoxide anions, hydrogen peroxide and hydroxyl radicals, that can modify important cellular macromolecules and initiate or accelerate diseases. The formation of reactive oxygen species can occur as part of many cellular processes including mitochondrial respiration, immune cell responses, cell injury, heat, radiation, or from metabolism of drugs and other chemicals. Reactive oxygen species are thought to be involved in almost all disease processes and the ageing process. For example, peroxynitrite is found to be a particularly damaging agent in diabetic retinopathies.

Current evidence reveals a paradox in the manipulation of reactive oxygen species for therapies. For example, boosting the levels of reactive oxygen species has proved beneficial in some maladies while scavenging reactive oxygen species with antioxidants is effective in others.

Most of the attempted treatments of ocular afflictions and cancers with antioxidants have used oral administrations of antioxidants with moderate to poor results. The NIH AREDS study, completed in 2001, involving high oral doses of antioxidants and zinc, showed some inhibition of the progression of macular degeneration but no protective effect on cataract formation. High oral doses of vitamin C have been dismissed as being therapeutic in cancer treatment, because even massive oral doses of ascorbates could not yield the therapeutic level achieved by intravenous or intraperitoneal injection. Thus, there is a need for minimally invasive injectable or implantable sustained release antioxidant formulations to maintain intraocular or intratumoral therapeutic levels of antioxidants.

SUMMARY

This present invention provide for effective novel therapies involving antioxidants to scavenge reactive oxygen species in the eye and in tumors. More specifically, the present invention provides for novel liquid and solid, sustained release formulations of biocompatible, biodegradable excipients containing antioxidants for intraocular or intratumoral injection or implantation as novel methods of treatment of ocular afflictions and cancer. The body and its cells have several mechanisms to control the effects of reactive oxygen species. The general term of such mechanisms is antioxidants. Antioxidants are enzymes, substances produced in the body, or substances that are found only in food.

An aspect of the present invention provides for the treatment of ocular disorders or tumors/cancers by administering formulations for sustained release of antioxidants at or near the site in need of treatment. Such antioxidant treatment can be used alone as a primary therapy, or in combination with other therapies to enhance the therapeutic benefits of other medical treatments.

An embodiment of the present invention provides for a method of treating an ocular disorder comprising administering to the eye a sustained release formulation of at least one antioxidant. In some embodiments, the ocular disorder is glaucoma, cataracts, or retinal degeneration. The administration can be done by injection or implantation. For use in the eye, the composition is a unit dosage formulation of about 5 µl to about 100 µl that can administered into the subconjunctiva, periocular space, retrobulbar in the orbit, episclera, intracornea, intrasclera, anterior chamber, anterior segment, posterior chamber, posterior segment, vitreous cavity, subretinal space, suprachorodial segment or intraretinal area of the eye. Liquid or gel formulations, upon initial injection, maintain monolithic integrity in a liquid or gel state.

Another embodiment of the present invention provides for an in situ method of treating a tumor comprising injecting or implanting into the tumor a sustained release formulation of at least one antioxidant.

DESCRIPTION OF THE DRAWINGS

FIG. 1 presents schematic structures of tocopheryl esters with ascorbic acid and glutathione.

FIG. 7C shows tissue analysis, H/E section, of a tumor treated once with sustained release astaxanthin formulation, which shows marked necrosis and disruption of tumor architecture. X16.

DETAILED DESCRIPTION

Figure 1A:
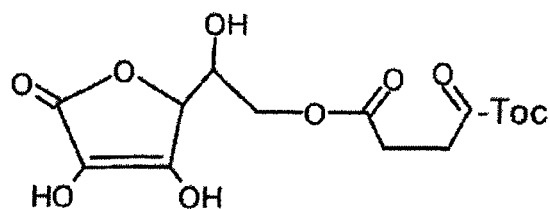
FIG. 1A shows 6-O-L-ascorbyl ester with tocopheryl-hemisuccinate.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention provides for novel liquid and solid, sustained release formulations of biocompatible, biodegradable excipients containing antioxidants for intraocular and intratumoral injection or implantation as novel methods of treatment of ocular afflictions and cancer. The instant formulations maintain a single monolithic shape at the site of their placement. That is, they do not break up as a multitude of smaller droplets or particles that migrate away from their intended point of placement or by virtue of a resultant increase in surface area greatly alter the intended release rate of the antioxidant content. The present antioxidant therapies that are easily manipulated and injected or implanted by qualified medical practitioners. The formulations deliver therapeutic and non-toxic levels of antioxidants over the desired extended time frame, primarily at the site of implantation. The formulations are both biocompatible and biodegradable, and disappear harmlessly after delivering active agent to the desired site. The duration of antioxidant delivery can be as short as a few days to many months and up to one year or longer, and the matrix gradually and safely dissipates over time so that there is no need to remove it.

Accumulating evidence points to free radical reactive oxygen species (ROS) initiating glaucoma, cataracts, and retinal degradations. Lou, 22 Prog. Retin. Eye Res. 657 (2003); Guajardo et al., 41 J. Pineal Res. 201 (2006); Winkler et al., Mol. Vis. 32 (1999). The evidence also points to ROS being involved in the angiogenesis used by tumor cells to sustain their growth. Roy et al., Free Rad. Bio. Med. 180 (2008); Storz, 1 Front Biosci. 1881 (2005). Scavenging ROS with nutritional antioxidants has not been particularly successful. Intravenous (iv) or intraperitoneal (ip) injections of antioxidants (ascorbates) have shown promise in restraining tumor growth.

ROS, as shown in the following table, include superoxide anions, hydrogen peroxide, and hydroxyl radicals:

| Oxidant | Description |
| --- | --- |
| $O^{2-}$ superoxide anion | One-electron reduction state of $O_2$, formed in many autoxidation reactions and by the electron transport chain. Rather unreactive, but can release $Fe^{2+}$ from iron-sulfur proteins and ferritin. Undergoes dismutation to form $H_2O_2$ spontaneously or by enzymatic catalysis and is a precursor for metal-catalyzed •OH formation. |
| $H_2O_2$ hydrogen peroxide | Two-electron reduction state, formed by dismutation of •$O_{2-}$ or by direct reduction of $O_2$. Lipid soluble and thus able to diffuse across membranes. |
| •OH hydroxyl radical | Three-electron reduction state, formed by Fenton reaction and decomposition of peroxynitrite. Extremely reactive, will attack most cellular components. |
| ROOH organic hydroperoxide | Formed by radical reactions with cellular components such as lipids and nucleobases. |
| RO•alkoxy and ROO•peroxy radicals | Oxygen centred organic radicals. Lipid forms participate in lipid peroxidation reactions. Produced in the presence of oxygen by radical addition to double bonds or hydrogen abstraction. |
| HOCl hypochlorous acid | Formed from $H_2O_2$ by myeloperoxidase. Lipid soluble and highly reactive. Will readily oxidize protein constituents, including thiol groups, amino groups and methionine. |
| ONOO— peroxynitrite | Formed in a rapid reaction between •$O_{2-}$ and NO•. Lipid soluble and similar in reactivity to hypochlorous acid. Protonation forms peroxynitrous acid, which can undergo homolytic cleavage to form hydroxyl radical and nitrogen dioxide. |

Additionally, it is known that $H_2O_2$ and other ROS initiate glaucoma, cataracts, macular degeneration, and retinal degenerations. Cui & Lou, 57 Exp. Eye Res. 157 (1993); Miyoshi et al., 103 P.N.A.S. 1727 (2006); Barbazetto et al., 78 Exp. Eye Res. 917 (2004). One important example is proliferative diabetic retinopathy (PDR), in which excessive levels of glucose in the blood stream lead to ROS that enter the vitreous and damage the retina. One study revealed that the ROS levels in the vitreous of PDR patients ranged from 5 to 35 μmoles/ml. Augustin et al., 12 Eur. J. Ophthalmol. 94 (2002). Those patients who poorly controlled their blood glucose levels had the highest ROS levels. It is also well known that the normal vitreous contains much higher levels of ascorbate (2 mM) (Takano et al., 16 Current Eye Res. 589-94 (1997)), than the plasma (0.15 mM) (Chen et al., 104 P.N.A.S. 8749 (2007)). Very likely this elevated level is needed to protect eye tissues from the extraordinary corrosive level of free radical chemistries induced by the eye's exceptional exposure to ultraviolet light and oxygen. Indeed, $H_2O_2$ induces VEGF production by the body (Stone & Collins, 9 Endothelium 231 (2002)), and vascularization is a hallmark of age-related macular degeneration (AMD). Specific novel antioxidant sustained release formulations provide for effective and cheap therapies for AMD, PDR, glaucoma, and cataracts.

Intratumoral injection of sustained release antioxidant formulations is another application for antioxidant sustained release formulations. There is accumulating evidence that elevated levels of in situ ascorbate will shrink tumors. Chen et al., 102 P.N.A.S. 13604 (2005). Alpha-tocopheryl succinate has been found to inhibit a variety of tumor cells. Shiau et al., 281 J. Bio. Chem. 11819 (2006); Prasad et al., 22 J. Am. Coll. Nutr. 108 (2003). So too does resveratrol (Shakibaei et al., 24 Mol. Nutr. Food Res. 2783 (2009); Aggarwal et al., 53 Anticancer Res. 115 (2004).

Without being bound by theory, two mechanisms have been proposed for how ascorbate or other antioxidants kill cancer cells. One mechanism involves $H_2O_2$ signaling. Although $H_2O_2$ above certain levels is quite cytotoxic, it has become apparent that low levels of $H_2O_2$ are intentionally generated by most all living organisms, especially vertebrates, as signaling messengers for a variety of important cellular functions. See Stone & Yang, 8 Antioxidants & Redox Signaling 243 (2006). Signaling-levels of $H_2O_2$ have been shown to induce VEGF production. Stone & Collins, 9 Endothel. 231 (2002); Ushio-Fukai & Alexander, 264 Mol. Cell. Biochem. 85 (2004). It also has been shown that cancer cells secrete high levels of $H_2O_2$ (up to 0.5 nanomoles/$10^4$ cells/hr) to induce angiogenesis for their survival. Ushio-Fukai & Nakamura, 266 Cancer Lett. 37 (2008); Statrowski & Nathan, 51 Cancer Res. 794 (1991). Thus, the present embodiments provide for the in situ injection of an antioxidant sustained release formulation that scavenges $H_2O_2$ and ROS that will effectively starve the tumor. See, e.g., Example 5.

A second proposed mechanism for the ability of ascorbate or other antioxidants to kill cancer cells involves selective $H_2O_2$ cytotoxicity. Both in vitro and in vivo experiments have demonstrated that intraperitoneal or intravenous injections of vitamin C that boost plasma levels of ascorbate to >2 mM can selectively kill a wide variety of cancer cells without harming normal cells. Chen et al., 2002. It is proposed that at these high levels ascorbate becomes pro-oxidative and acts as a prodrug for the formation of $H_2O_2$ levels selectively toxic to cancer cells. No matter by which mechanism (or both) antioxidants lead to cancer cell death, in situ sustained administrations of antioxidants may prove worthy treatments, and the sustained release formulations of the present invention are particularly advantageous to such therapies.

The formulations of this invention provide for the sustained delivery of therapeutic and non-toxic levels of antioxidants at the site of the indication (i.e., eye or tumor) over periods of at least 1 day, about 4 days, about 1 week, several weeks, about 1 year, or longer, inclusive. Liquid formulations are delivered by injection and solid formulations are implanted. These formulations are both biocompatible and biodegradable, and disappear harmlessly after the delivery of the antioxidants to the desired site. In some embodiments, the formulations are novel combinations of one or more biocompatible and biodegradable excipients with one or more of antioxidants. A strategy employed here is to select or synthesize new antioxidants having low water solubility so that the antioxidant is not flushed away too soon by the aqueous environment of the body. Also, low water soluble antioxidants generally have a lipophilicity that aids in their permeating cell membranes.

Non-polymeric excipients that provide for sustained release for use in the present invention include, but are not limited to, at least one biodegradable, biocompatible excipient such as benzyl benzoate; esters of benzoic acid with straight, branched, or cyclic chain aliphatic alcohols having one to twenty carbon atoms wherein one of the hydrogen atoms on the aliphatic chain is replaced with a hydroxyl group (e.g., such alcohols as methanol, ethanol, n-propanol, i-propanol, n-butanol, i-butanol, s-butanol, t-butanol, n-pentanol, i-pentanol, neo-pentanol, n-hexanol, cyclohexanol, n-heptanol, n-octonol, n-nonanol, n-decanol, and the like); diethylene glycol dibenzoate; triethylene glycol dibenzoate; dimethyl sulfone; dimethyl sulfozide; mono, di, and tri esters of O-acetylcitric acid or O-propionylcitric acid or O-butyrylcitric acid with $C_1$ to $C_{10}$ straight and branched chain aliphatic alcohols; the mono, di, and tri esters of citric acid with $C_1$ to $C_{10}$ straight and branched chain aliphatic alcohols; triethyl citrate (TEC); acetyl triethyl citrate (ATEC); tri-n-butyl citrate; acetyl tri-n-butyl citrate; acetyl tri-n-hexyl citrate; butyryl tri-n-hexyl citrate; and/or citric acid ethers; d-alpha-tocopherol; d,l-alpha-tocopherol; d-beta-tocopherol; d,l-beta-tocopherol; d-eta-tocopherol; d,l-eta-tocopherol (including acetate, hemisuccinate, nicotinate, and succinate-PEG ester forms of each of the foregoing); tocopheryl acetate; tocotrienol isomers, and their esters; dimethyl sulfone; dimethyl sulfoxide; or MIGLYOL® neutral oil (Sasol Germany GmbH, Witten, Germany). See, e.g., U.S. Pat. No. 7,906,136, U.S. Pat. No. 7,560,120, U.S. Pat. No. 6,960,346; U.S. Patent Pub. 2011/0111006.

The non-polymeric excipient is typically present in the formulation of the present invention in an amount wherein the amount of the excipient is sufficient to dissolve, disperse, emulsify, or suspend the entire amount of the active agent in the pharmaceutical composition. In some cases, the concentration of excipient in the composition can be higher than the concentration of any other constituent in the composition. In some embodiments, the excipient itself can be considered an antioxidant (i.e., a drug), as may be the case for tocopherol or tocopheryl acetate depending on context.

Biocompatible, biodegradable polymers that may be used as an excipient to effect sustained release include dibenzoate esters of poly(oxyethylene)diols of up to about 400 mwt; propylene glycol dibenzoate; dipropylene glycol dibenzoate; tripropylene glycol dibenzoate; dibenzoate esters of poly(oxypropylene)diols of up to about 3000 mwt; poly(oxypropylene)diols of up to about 3000 mwt; liquid to semisolid polycarbonate oligomers, such as, but not limited to, those prepared by the polymerization of trimethylene carbonate [poly(1,3-propanediol carbonate)] or the ester exchange polymerization of diethylene carbonate with aliphatic diols or polyoxyalkane diols [poly(di-1,2-propylene glycol carbonate) or poly(tri-1,2-propylene glycol carbonate)]. See, e.g., U.S. Pat. No. 7,906,136, U.S. Pat. No. 7,560,120, and U.S. Pat. No. 6,960,346; U.S. Patent Pub. 2011/0111006.

In some embodiments, a non-polymeric liquid excipient may be mixed with a small amount (≤ about 10%) of at least one biodegradable, biocompatible poly(D,L-lactide) (PLA) and/or poly(D,L-lactide-co-glycolide) (PLGA) polymer; wherein the ratio of non-polymeric excipient:polymer is about 90:10 to about 99:1, inclusive.

Liquid, gel, and solid sustained release antioxidant formulations can be implanted, for example, by trocar or by needle introduction. The formulation can be placed into the eye by (intraocular) (such as the chambers such as the anterior segment and posterior segment of the eye, see U.S. Pat. No. 7,906,136); intratumoral injection (such as into the prostate tumor, typically using a procedure similar to that described by Jackson et al., 60 Cancer Res., 4146 (2000)); or intratumoral injection into inoperable tumors (such as gliomas) in the brain (typically using a procedure similar to that described by Emerich et al., 17 Pharm. Res. 767 (2000)). The sustained release antioxidant formulations of the present invention may be implanted or injected at or near the site of action. This may be useful when it is used, for example, in treating ocular conditions or primary tumors.

The formulations of the present embodiments may provide for sustained release of the antioxidants for at least 4 days, at least 7 days, at least 14 days, at least 20 days, at least 30 days, at least 40 days, at least 50 days, at least 60 days, at least 112 days, at least 365 days, or longer, inclusive.

Figure 1B:
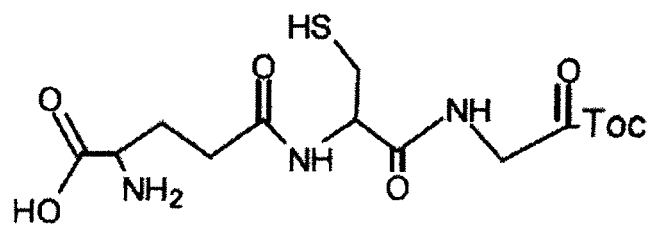
FIG. 1B shows tocopheryl ester with reduced glutathione.
Figure 1C:
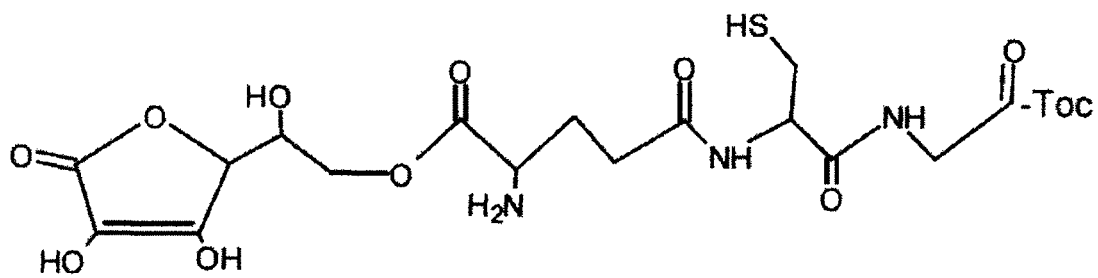
FIG. 1C presents 6-O-L-ascorbyl ester with reduced glutathione-tocopheryl ester.
Figure 1D:
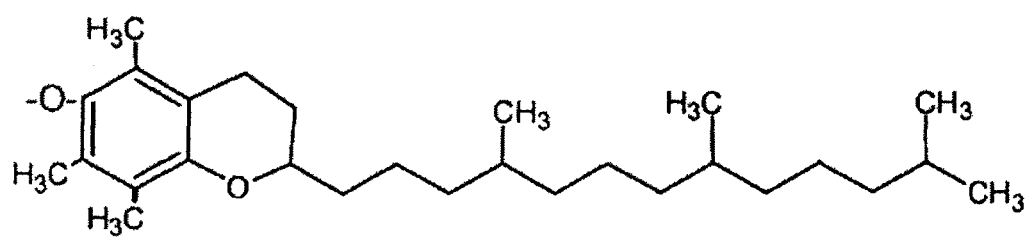
FIG. 1D shows d or dl-alpha-isomers of tocopheryl.

Antioxidants suitable for use in the present invention include, but are not limited to, ascorbic acid, Na ascorbate, K ascorbate, Ca ascorbate, Mg ascorbate, Zn ascorbate; 6-O-esters of ascorbic acid with $C_2$ to $C_{20}$ straight, branched, saturated and unsaturated fatty acids: 6-O-lauroyl ascorbate, 6-O-myristoyl ascorbate, 6-O-oleoyl ascorbate, 6-O-palmitoyl ascorbate, 6-O-linoleoyl ascorbate, 6-O-stearoyl ascorbate; 6-O-ester of ascorbic acid with d, or dl-α-tocopheryl hemisuccinate as shown in FIG. 1A; 6-O-esters of ascorbic acid with reduced glutathione and d, or dl-α-tocopherols as shown in FIG. 1C; reduced glutathione and glutathione ester of reduced glutathione with d or dl-α-tocopherol as shown in FIG. 1B; d and dl-tocopherol (α, β, γ, δ isomers) and the acetate, hemisuccinate, nicotinate, and succinate-PEG ester (TPGS) derivatives of the foregoing tocopherol isomers; superoxide dismutase; β-carotine; melatonin; trans resveratrol; trolox; coenzyme Q; catalase; various peroxidases; cysteine, ester of cysteine with ethanol, HCl salt of the ester of cysteine with ethanol, the salt of ascorbic acid with the ester of cysteine with ethanol, the d or dl-α-tocopherol-hemisuccinate salt of the ester of cysteine with ethanol, the ester of cysteine with d, or dl-α-tocopherol, N-acetylcysteine, Na, K, Ca, Mg, Zn salts of N-acetylcysteine, ester of N-acetyl cysteine with ethanol or d, or dl-α-tocopherol; l-carnitine; l-carnitine acetate; retinal; tretinoin; timolol; lutein; thyroxine; purroloquinolone; pyrroloquinolone; probucol; captopril; desferal $Mn^{+3}$; uric acid; erithorbic acid and its salts; α-lipoic acid; lycopene; astaxanthin; zeaxanthin; ferulic acid; quercetin; eugenol and isoeugenol; prostaglandins; latanoprost, bimatoprost, travoprost; (−)-epicatechin; (−)-epigallocatechin gallate; butylated hydroxytoluene; butylated hydroxyanisole; rutin; fisetin; sulfite and bisulfite salts (Na, K, Ca, Mg).

It appears that ascorbate, reduced glutathione, tocopherol, and superoxide dismutase are the body's front line antioxidants in the eye and possibly elsewhere in the body. The antioxidant tocopherol is an ideal lipid soluble ligand to attach to ascorbate and/or reduced glutathione and/or cysteine. These compounds are shown in FIGS. 1A to 1C.

It is contemplated that the described sustained release formulations can also be administrated along with the large array of other therapeutic agents to elicit synergistic enhancements of their therapies. A partial, but non-limiting, list of the therapeutic agents includes Steroidal Anti-inflammatories, including dexamethasone, triamcinolone acetonide; Nonsteroidal Anti-inflammatories, including celcoxib, ibuprofin, naproxin, diclofenac; AntiVEGF Agents, including bevacizumab, ranibizumab; Immune Response Moderators, including cyclosporin A, rapamycin; Antimicrotubule Agents, including the taxoids, vincristine; Alkylalating Agents, including temolzolomide, cisplatin; Anti-glaucoma Agents, including timolol, latanoprost; Testosterone Reduction, including fenasteride, dutasteride; Anti-infective Agents, including ciprofloxacin, the penicillins; Anti-virals, including acyclovir, ganciclovir; and Anti-HIV Agents, including etravirine, emtricitabine.

Another factor that may be considered in the selection of antioxidants in the present invention is the known concentrations of indigenous antioxidants in the human eye's vitreous, as shown, for example in the following table:

| Ascorbic Acid | FW 176 | 400 µg/ml | 2.3 µmoles/ml | [1] |
|---|---|---|---|---|
| α-Tocopherol | FW 431 | 30 µg/ml | 0.07 µmoles/ml | [2] |
| Reduced Glutathione | FW 307 | 30 µg/ml | 0.1 µmoles/ml | [3] |
| Melatonin | FW 232 | 19 pg/ml | 0.08 pmoles/ml | [4] |

[1] Takano et al., 16 Curr. Eye Res. 584 (1997);
[2] Alvarez et al., 46 Am. J. Clin. Nutr. 481 (1987) (estimated from levels measured in the retina (3.0 µg/ml) and pigment epithelium & choroids (3.0 µg/ml));
[3] Micelli-Ferrari et al., 80 Br. J. Ophthalmol. 840 (1996) (estimate based on reduced glutathione in lens (100 nmoles/g));
[4] Stumer et al., 45 Forensic Sci. Int'l 171 (1990) (levels in infants). The level in NZW rabbits is 109 pg/ml. Kiuchi et al., 12 Curr. Eye Res. 181 (1993).

In the case of the thiol antioxidant, but quite water soluble (reduced) glutathione, there are often no readily available derivatives having the desired low water solubility. Thus, novel glutathione derivatives may be employed in the formulations of the present invention. More practical is the use of the active segment in glutathione, cysteine. The ethyl ester-.HCl of this amino acid is relatively inexpensive and readily available. The free base form of the ethyl ester may be converted it to the salt with α-tocopheryl hemisuccinic acid, which appears to have low water solubility, and may be substituted for the tocopherol succinate formulations of some of the present embodiments. Additionally, the antioxidants of the present invention include the free acid form of tocopheryl hemi-succinate with the free base forms of esters of l-cysteine.

Figure 4:
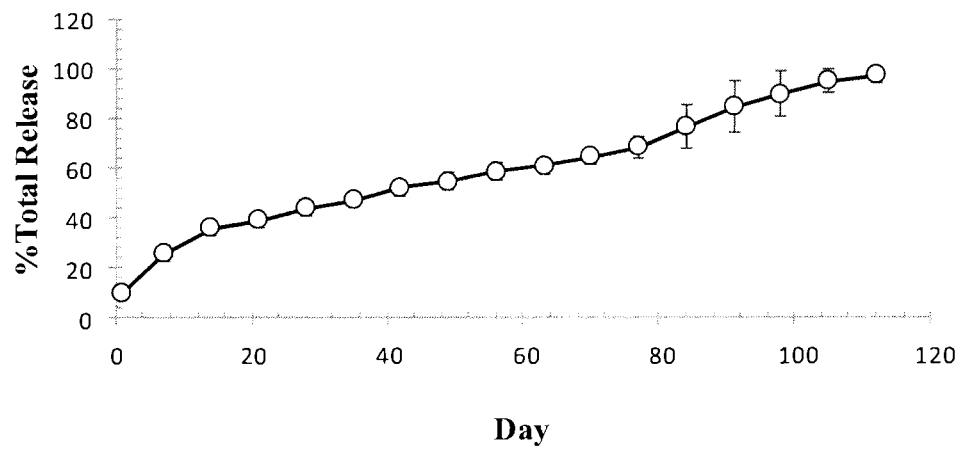
FIG. 4 is a graph showing in vitro release of timolol from a sustained release formulation consisting of 20% timolol in 80% 1:1 ATEC:EA. X-axis: Days; Ave (N=6).
Figure 5:
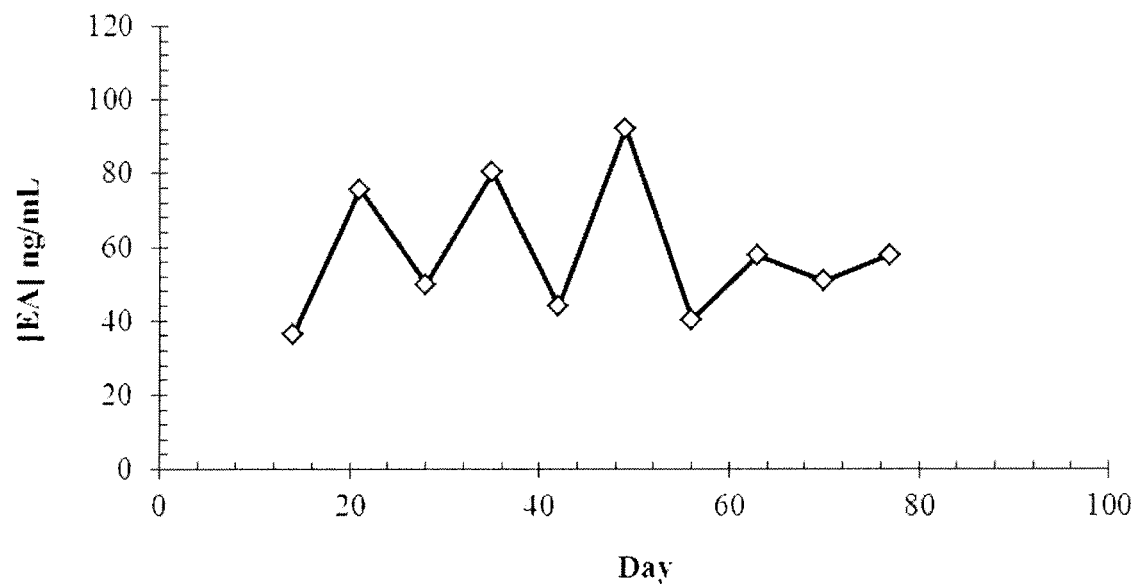
FIG. 5 is a chart showing the level of vitamin E acetate (EA) in the vitreous humor (ng/mL EA determined by LC/MS/MS) following injection of 50 µL into the vitreous. The first time point is day 15 post-injection.

Additionally, timolol has been used as a beta-blocker in the treatment of glaucoma. Recently, it has been hypothesized that timolol exerts a direct antioxidant activity protecting human endothelial cells from oxidative stress, and that this antioxidant activity is involved in the therapeutic effect of this drug against glaucoma. Izzotti et al., 22 Eye 445 (2008). Thus, in some embodiments, the sustained release formulation includes timolol as an antioxidant component (see, e.g., FIG. 4).

Further particular embodiments combine antioxidants, or combine antioxidants, and additional therapeutic agents in a formulation. Such additional agents include, for example, an anti-inflammatory agent. For example, a particular formulation includes timolol combined with a corticosteroid such as dexamethasone or triamcinolone in a tocopherol excipient or a tocopherol:citrate excipient. As another example, a particular formulation includes timolol and reservatrol in a tocopherol excipient, a tocopherol:citrate, or a citrate:PLGA excipient. The sustained release antioxidant formulations may also be used in conjunction with other therapies, such as anti-cancer treatments.

A "disorder" is any condition that would benefit from treatment with, for example, a sustained release antioxidant. This includes chronic and acute disorders or diseases including those pathological conditions which predispose the subject to the disorder in question. Non-limiting examples of disorders to be treated herein include tumors or cancers.

Thus, an embodiment of the present invention provides for the use of sustained release antioxidant formulations of treating tumors, of inhibiting tumor/cancer growth, prolonging the life of a subject afflicted with a tumor, or of reducing one or more symptoms associated with tumors. One aspect of the invention provides a method of treating a tumor/cancer in a subject in need of such treatment, the method comprising administering to the subject a therapeutically effective amount of a sustained release antioxidant. "Tumor" refers to all neoplastic cell growth and proliferation, whether malignant or benign, and all pre-cancerous and cancerous cells and tissues.

"Treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a disorder such as, but not limited to, ocular edema or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

A "subject" as used herein refers to a mammal or bird, and mammal includes a human. Examples of subjects include humans, non-human primates, rodents, domestic livestock, dogs, cats, or birds. Individuals and patients are also subjects herein.

In general, the goal of treatment is reducing the size of a tumor or level of an antigen, or inhibiting the activity of a target, as measured using a suitable in vitro, cellular or in vivo assay. In particular, decreasing the biological activity of a target, antigen or tumor, as measured using a suitable in vitro, cellular or in vivo assay (which will usually depend on the target involved), by at least 5%, 10%, 25%, 50%, 60%, 70%, 80%, or 90%, or 100%, inclusive, as compared with an equivalent untreated control. A decrease refers to a statistically significant decrease. For the avoidance of doubt, a decrease will be at least 5% relative to a reference, such as at least 5%, 10%, 20%, 30%, 40%, 50%, 60%, 70%, 80%, 90%, or more, up to and including 100%, inclusive. Reduce or inhibit can refer to, for example, the symptoms of the disorder being treated, such as the presence or size of the primary tumor or a reduction in ocular pressure.

The data obtained from the cell culture assays and animal studies can be used in formulating a range of dosage for use in humans. The dosage of such compounds lies preferably within a range of concentrations that include the $ED_{50}$ with little or no toxicity. The dosage may vary within this range depending upon the dosage form employed, e.g., injectable liquid or gel or implantable solid. For any antioxindant(s) used in the method of the invention, the therapeutically effective dose can be estimated initially from cell culture assays.

To test the sustained release formulations of the invention for their ability to treat tumors in vivo, tumors can be explanted into nude mice (i.e., athymic mice). Various xenograft models are known in the art. After the tumors are established in mice, the sustained release antioxidant formulations are administered to the mice in order to test for whether the agents can diminish the tumors or prolong median survival of the animals.

An "effective amount" as used herein is any amount that is sufficient either to promote the occurrence of a desired outcome or condition, or to reduce or inhibit the occurrence of an undesired outcome or condition. In some instances a desired outcome or condition is an ideal that represents one end of a spectrum of possible outcomes or conditions. In such instances an effective amount is any amount associated with an outcome or condition that is closer to the desired ideal than would be achieved or observed without the effective amount. Thus, an effective amount promotes the occurrence of a desired outcome or condition, but it need not achieve an ultimate endpoint.

In some embodiments the subject has cancer or is at risk of having cancer. A "cancer" as used herein refers to an uncontrolled growth of cells which interferes with the normal functioning of the bodily organs and systems. A subject that has a cancer is a subject having objectively measurable cancer cells present in the subject's body. A subject at risk of having a cancer is a subject that is predisposed to develop a cancer. Such a subject can include, for example, a subject with a family history of or a genetic predisposition toward developing a cancer. A subject at risk of having a cancer also can include a subject with a known or suspected exposure to a cancer-causing agent.

Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas and sarcomas. Additionally, the cancers to be treated may be refractory cancers.

The formulations and methods of the invention in certain instances may be useful for replacing existing surgical procedures or drug therapies, although the present invention is also useful in improving the efficacy of existing therapies for treating such conditions. Accordingly, combination therapy may be used to treat the subjects that are undergoing or that will undergo a treatment for, inter alia, eye disease or tumor/cancer. For example, the agents of the present invention can be administered in conjunction with anti-microbial agents or anti-proliferative agents. The agents of the invention also can be administered in conjunction with other immunotherapies, such as with antigens, adjuvants, immunomodulators, or passive immune therapy with antibodies. The agents of the invention also can be administered in conjunction with nondrug treatments, such as surgery, radiation therapy or chemotherapy. The other therapy may be administered before, concurrent with, or after treatment with the agents of the invention. There may also be a delay of several hours, days and in some instances weeks between the administration of the different treatments, such that the agents of the invention may be administered before or after the other treatment.

In some embodiments the method according to this aspect of the invention further involves administering to the subject an anti-tumor medicament. As used herein, an "anti-tumor medicament" or, equivalently, a "cancer medicament", refers to an agent which is administered to a subject for the purpose of treating a cancer. As used herein, "treating cancer" includes preventing the development of a cancer, reducing the symptoms of cancer, and/or inhibiting the growth of an established cancer. The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer. In other aspects, the cancer medicament is administered to a subject at risk of developing a cancer for the purpose of reducing the risk of developing the cancer.

Various types of medicaments for the treatment of cancer are described herein or are otherwise known in the art. Cancer medicaments are typically classified as chemotherapeutic agents, immunotherapeutic agents, cancer vaccines, hormone therapy, and biological response modifiers. Additionally, the methods of the invention are intended to embrace the use of more than one cancer medicament along with the sustained release antioxidants of the present invention. As an example, where appropriate, the sustained release antioxidant formulation can be administered with a both a chemotherapeutic agent and an immunotherapeutic agent. Alternatively, the cancer medicament can embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

Cancer medicaments function in a variety of ways. Some cancer medicaments work by targeting physiological mechanisms that are specific to tumor cells. Examples include the targeting of specific genes and their gene products (i.e., proteins primarily) which are mutated in cancers. Such genes include but are not limited to oncogenes (e.g., Ras, Her2, bcl-2), tumor suppressor genes (e.g., EGF, p53, Rb), and cell cycle targets (e.g., CDK4, p21, telomerase). Cancer medicaments can alternately target signal transduction pathways and molecular mechanisms which are altered in cancer cells. Targeting of cancer cells via the epitopes expressed on their cell surface is accomplished through the use of monoclonal antibodies. This latter type of cancer medicament is generally referred to as immunotherapy.

For example, the agent may be administered together with any one or more of the chemotherapeutic drugs known to those of skill in the art of oncology. A "chemotherapeutic agent" is a chemical compound useful in the treatment of cancer. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, 33 Chem. Intl. Ed. Engl. 183 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® doxorubicin (and morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishes such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Prods., Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE®, a Cremophor-free, albumin-engineered nanoparticle formulation of paclitaxel (Celgene Corp.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; XELODA® (capecitabine); ibandronate; CAMPTOSAR® (irinotecan, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above; and all approved and experimental anti-cancer agents listed in WO 2005/017107. The agent can be administered in combination with 1, 2, 3 or more of these agents, e.g., in a standard chemotherapeutic regimen.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® (toremifene); aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane), formestanie, fadrozole, RIVISOR® (vorozole), FEMARA® (letrozole), and ARIMIDEX® (anastrozole); and anti-androgens such as flutamide, nilutamide, bicalutamide, leuprolide, and goserelin; as well as troxacitabine (a 1,3 dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME™ ribozyme) and a HER2 expression inhibitor; immunotherapies such as PROLEUKIN® (aldesleukin) rIL-2, ALLOVACTIN® DNA-based immunotherapic, LEUVECTIN® IL-2 gene therapy; vaccines such as Vaxid® DNA vaccine; LURTOTECAN® camptothecin topoisomerase 1 inhibitor; abarelix gonadotropin-releasing hormone antagonist; and pharmaceutically acceptable salts, acids or derivatives of any of these.

Additional chemotherapeutic agents which are currently in development or in use in a clinical setting include, without limitation: 5-FU Enhancer, 9-AC, AG2037, AG3340, Aggrecanase Inhibitor, Aminoglutethimide, Amsacrine (m-AMSA), Angiogenesis Inhibitor, Anti-VEGF, Asparaginase, Azacitidine, Batimastat (BB94), BAY 12-9566, BCH-4556, Bis-Naphtalimide, Busulfan, Capecitabine, Carboplatin, Carmustaine+Polifepr Osan, cdk4/cdk2 inhibitors, Chlorombucil, CI-994, Cisplatin, Cladribine, CS-682, Cytarabine HCl, D2163, Dactinomycin, Daunorubicin HCl, DepoCyt, Dexifosamide, Docetaxel, Dolastain, Doxifluridine, Doxorubicin, DX8951f, E 7070, EGFR, Epirubicin, Erythropoietin, Estramustine phosphate sodium, Etoposide (VP16-213), Farnesyl Transferase Inhibitor, FK 317, Flavopiridol, Floxuridine, Fludarabine, Fluorouracil (5-FU), Flutamide, Fragyline, Gemcitabine, Hexamethylmelamine (HMM), Hydroxyurea (hydroxycarbamide), Ifosfamide, Interferon Alfa 2a, Interferon Alfa-2b, Interleukin-2, Irinotecan, ISI 641, Krestin, Lemonal DP 2202, Leuprolide acetate (LHRH-releasing factor analogue), Levamisole, LiGLA (lithium-gamma linolenate), Lodine Seeds, Lometexol, Lomustine (CCNU), Marimistat, Mechlorethamine HCl (nitrogen mustard), Megestrol acetate, Meglamine GLA, Mercaptopurine, Mesna, Mitoguazone (methyl-GAG; methyl glyoxal bis-guanylhydrazone; MGBG), Mitotane (o.p'-DDD), Mitoxantrone, Mitoxantrone HCl, MMI 270, MMP, MTA/LY 231514, Octreotide, ODN 698, OK-432, Oral Platinum, Oral Taxoid, Paclitaxel (TAXOL®), PARP Inhibitors, PD 183805, Pentostatin (2' deoxycoformycin), PKC 412, Plicamycin, Procarbazine HCl, PSC 833, Ralitrexed, RAS Famesyl Transferase Inhibitor, RAS Oncogene Inhibitor, Semustine (methyl-CCNU), Streptozocin, Suramin, Tamoxifen citrate, Taxane Analog, Temozolomide, Teniposide (VM-26), Thioguanine, Thiotepa, Topotecan, Tyrosine Kinase, UFT (Tegafur/Uracil), Valrubicin, VEGF/b-FGF Inhibitors, Vinblastine sulfate, Vindesine sulfate, VX-710, VX-853, YM 116, ZD 0101, ZD 0473/Anormed, ZD 1839, ZD 9331. Biological agents include, for example, antibody-derived agents, RNAi, ribozymes, cytokines, chemokines, ligands, or vaccines.

Other agents with which the sustained release antioxidants can be administered include biologics such as monoclonal antibodies, including Herceptin® (trastuzumab) against the HER2 antigen, Avastin® (bevacizumab) against VEGF, antibodies to the EGF receptor such as Erbitux® (cetuximab), or an anti-FGF mAb, as well as small molecule anti-angiogenic or EGF receptor antagonist drugs such as IRESSA™ (gefitinib) and Tarceva® (erlotinib); or antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2. In addition, the agent can be administered together with any form of radiation therapy including external beam radiation, intensity modulated radiation therapy (IMRT) and any form of radiosurgery including Gamma Knife, Cyberknife, Linac, and interstitial radiation (e.g. implanted radioactive seeds, GliaSite balloon). In one embodiment, the sustained release antioxidant with or without additional agents is administered during a surgical procedure, such as, for example, during the removal of a tumor or a tumor biopsy.

Examples of angiogenic inhibitors that can be used in combination with the CEACAM1 inhibitors, such as recombinant anti-CEACAM1 antibodies and portions thereof, described herein include, but are not limited to: direct angiogenesis inhibitors, Angiostatin, Bevacizumab (Avastin®), Arresten, Canstatin, Combretastatin, Endostatin, NM-3, Thrombospondin, Tumstatin, 2-methoxyestradiol, cetuximab (Erbitux®), panitumumab (Vectibix®), trastuzumab (Herceptin®) and Vitaxin; and indirect angiogenesis inhibitors: ZD1839 (Iressa), ZD6474, OSI774 (Tarceva), CI1033, PKI1666, IMC225 (Erbitux), PTK787, SU6668, SU11248, Herceptin, and IFN-α, CELEBREX® (celecoxib), THALOMID® (Thalidomide), and IFN-α. In some embodiments, the angiogenesis inhibitors for use in the methods described herein include but are not limited to small molecule tyrosine kinase inhibitors (TKIs) of multiple pro-angiogenic growth factor receptors. The three TKIs that are currently approved as anti-cancer therapies are erlotinib (Tarceva®), sorafenib (Nexavar®), and sunitinib (Sutent®); inhibitors of mTOR (mammalian target of rapamycin) such as temsirolimus (Toricel™), bortezomib (Velcade®), thalidomide (Thalomid®), and Doxycyclin. anti-angiogenic factors such as alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C-X-C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronection (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-beta), vasculostatin, and vasostatin (calreticulin fragment). pamidronate thalidomide, TNP470, the bisphosphonate family such as amino-bisphosphonate zoledronic acid. bombesin/gastrin-releasing peptide (GRP) antagonists such as RC-3095 and RC-394041 (Bajol et. al., 90 British J. Cancer 245 (2004), anti-VEGF peptide RRKRRR (dRK6) (Yoo, 174 J. Immunol. 5846 (2005).

The agents of the invention also are used with nondrug treatments for cancer, such as with surgical procedures to remove the cancer mass, chemotherapy or radiation therapy. The nondrug therapy may be administered before, concurrent with, or after treatment with the agents of the invention. There may also be a delay of several hours, days and in some instances weeks between the administration of the different treatments, such that the agents of the invention may be administered before or after the other treatment.

Other cancer medicaments target cells other than cancer cells. For example, some medicaments prime the immune system to attack tumor cells (i.e., cancer vaccines). Still other medicaments, called angiogenesis inhibitors, function by attacking the blood supply of solid tumors. Because the most malignant cancers are able to metastasize (i.e., exit the primary tumor site and seed a distal tissue, thereby forming a secondary tumor), medicaments that impede this metastasis are also useful in the treatment of cancer. Angiogenesis inhibitors include basic FGF (b-FGF), VEGF, angiopoietins, angiostatin, endostatin, TNF-α, TNP-470, thrombospondin-1, platelet factor 4, CAI, and certain members of the integrin family of proteins. One category of this type of medicament is a metalloproteinase inhibitor, which inhibits the enzymes used by the cancer cells to exist the primary tumor site and extravasate into another tissue.

Immunotherapeutic agents are medicaments which derive from antibodies or antibody fragments which specifically bind or recognize a cancer antigen. The goal of immunotherapy is to augment a patient's immune response to an established tumor. One method of immunotherapy includes the use of adjuvants. Adjuvant substances derived from microorganisms, such as bacillus Calmette-Guérin, heighten the immune response and enhance resistance to tumors in animals. Additional examples of cancer immunotherapies which are currently being used or which are in development include but are not limited to RITUXAN® (rituximab) and IDEC-C2B8 (rituximab) anti-CD20 Mab, Panorex (Edrecolomab), 3622W94, anti-EGP40 (17-1A) pancarcinoma antigen on adenocarcinomas, HERCEPTIN® anti-Her2, Anti-EGFr, BEC2, anti-idiotypic-GD$_3$ epitope, OVAREX (oregovomab, MAb B43.13), anti-idiotypic CA125, 4B5, Anti-VEGF, RhuMAb, MDX-210, anti-HER-2, MDX-22, MDX-220, MDX-447, MDX-260, anti-GD-2, Quadramet, CYT-424, IDEC-Y2B8, ONCOLYM® MAb Lym-1, SMART™ M195 radiolabeled MAb, ATRAGEN® tretinoin, LDP-03, anti-CAMPATH, ior t6, anti CD6, MDX-11, OV103, ZENAPAX® daclizumab anti-Tac MAb, anti-IL-2 receptor, MELIMMUNE-2™, MELIMMUNE-1™, CEA-CIDE™ (labetuzumab), PRETARGET® radiolabeled MAb, NovoMAb-G2, TNT, anti-histone, Gliomab-H, GNI-250, EMD-72000, LymphoCide (epratuzumab) anti-CD22 MAb, CMA 676, Monopharm-C, ior egf/r3, ior c5, anti-FLK-2, SMART 1D10, SMART ABL 364, and IMMURAIT™-CEA.

As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

In some embodiments, the treatment with sustained release antioxidants can be accompanied with administering to the subject a cytokine. A "cytokine" refers to any of a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to interleukins IL-1, IL-2, IL-4, IL-5, IL-6, IL-7, IL-10, IL-12, IL-15, IL-18; granulocyte-macrophage colony-stimulating factor (GM-CSF); granulocyte colony-stimulating factor (G-CSF); interferons including interferon-alpha (IFN-α), interferon-beta (IFN-β), and interferon-gamma (IFN-γ); tumor necrosis factor (TNF), transforming growth factor-beta (TGF-β); FLT-3 ligand; and CD40 ligand.

Alternatively, and as indicated by medical condition, the treatment with sustained release antioxidants further involves administering to the subject an antibacterial, antiviral, antimycobial, antifungal, antiparasitic, or other antiinfective medicament.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As will be understood by those of ordinary skill in the art, the appropriate doses of antioxidants with or without additional agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

"Administering" the sustained release antioxidant of the present invention may be accomplished by any means known to the skilled artisan. Injection of liquid formulations into the eye is achieved via an injection needle having a relatively small gauge, typically 25 gauge, 27 gauge, 28 gauge, 30 gauge, 31 gauge, or smaller. Solid implants can be administered via trocar, needle trocar, or other methods known in the art. See, e.g., U.S. Pat. No. 7,906,136; U.S. Pat. No. 5,869,079; U.S. Pat. No. 7,625,582. Surgical implantation into the eye is known in the art as described in U.S. Pat. No. 6,699,493; U.S. Pat. No. 6,726,918; U.S. Pat. No. 6,331,313; U.S. Pat. No. 5,824,072; U.S. Pat. No. 5,766,242; U.S. Pat. No. 5,443,505; U.S. Pat. No. 5,164,188; U.S. Pat. No. 4,997,652; U.S. Pat. No. 4,853,224.

Pharmaceutical formulations may be conveniently presented in unit dosage form and may be prepared by any of the methods well known in the art of pharmacy. All methods include the step of bringing the antioxidant(s) into association with the biocompatible, bioerodable excipients of the present invention. In general, the formulations are prepared by uniformly and intimately bringing the antioxidant(s) into association with a liquid excipient, a finely divided solid excipient, or both, and then, if necessary, shaping the product. Formulations for injection or implantation may be presented in unit dosage form, e.g., in ampoules or in multi-dose containers.

This invention is further illustrated by the following non-limiting examples.

EXAMPLES

Example 1

Formulation Comprising Multiple Antioxidants

A composition consisting of antioxidants and biocompatible, biodegradable, sustained release excipients was formulated using potent, commercially available, USP quality antioxidants for ocular and tumor therapies. The formulation contained the following five antioxidants or their derivatives having low enough aqueous solubility to yield sustained release of therapeutic amounts:

| | |
|---|---|
| 6-O-palmitoyl-L-ascorbate | FW 415 |
| α-tocopheryl succinate | FW 531 |
| melatonin | FW 232 |
| resveratrol | FW 228 |
| astaxanthin | FW 597 |

The mixture contained 100 µmoles of each antioxidant:

| | |
|---|---|
| 6-O-palmitoyl-L-ascorbate | 41.5 mg |
| α-tocopheryl succinate | 53.1 |
| melatonin | 23.2 |
| resveratrol | 22.8 |
| astaxanthin | 59.7 |
| Total | 201 mg |
| | (0.5 mmoles total antioxidants) |

Example 2

Tocopheryl Acetate Levels In Vitreous Humor

Figure 2:
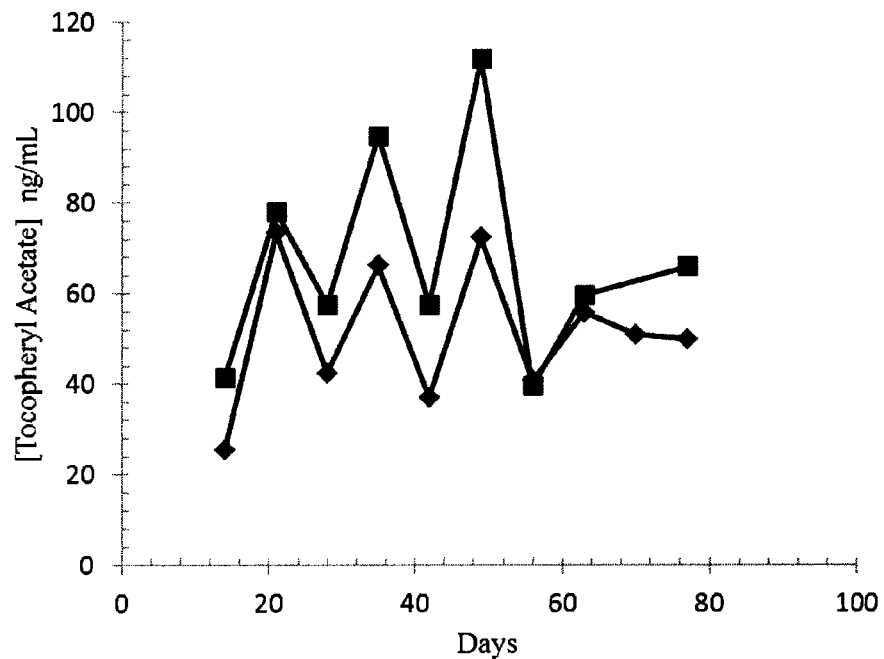
FIG. 2 is a graph showing in vivo tocopheryl acetate levels in the vitreous humor (posterior segment) following injection into the eye of either a 25 µL (♦) or 50 µL (■) unit dose.

Tocopheryl acetate (Vitamin E acetate) (USP grade) was Purchased from Letco Medical (Decatur, Ala.). For in-vivo study, Vitamin E acetate (25 µL or 50 µL) was injected into the posterior chambers of New Zealand White Rabbits. Vitreous samples were withdrawn weekly. Concentrations of tocopheryl acetate were determined using Liquid Chromatography Mass Spectrometer (LC/MS/MS): Mass Spectrometer, API 3200 system from AB Sciex and LC (DGU-20AD) from Shimazdu. The results are shown in FIG. 2.

Example 3

Release of a Stilbenoid from Sustained Release Formulations

Resveratrol (also called 3,5,4'-trihydroxy-trans-stilbene; trans-3,5,4'-Trihydroxystilbene; 3,4',5-Stilbenetriol; trans-Resveratrol; (E)-5-(p-Hydroxystyryl)resorcinol; and (E)-5-(4-hydroxystyryl)benzene-1,3-diol), is a stilbenoid, which is a type of natural phenol and a phytoalexin produced naturally by several plants, apparently to repel pathogens such as bacteria or fungi. Resveratrol is also found in the skin of red grapes and in other fruits. Resveratrol has also been produced by chemical synthesis or by biotechnological synthesis (metabolic engineered microorganisms) and is sold as a nutritional supplement derived primarily from Japanese knotweed. In animal experiments, anti-cancer, anti-inflammatory, blood-sugar-lowering, and other beneficial cardiovascular effects of resveratrol have been reported.

Formulations comprising resveratrol were prepared by mixing (by stirring) one portion of Resveratrol with nine portions of excipients (shown below):

| | % Drug/balance Excipient(s) |
|---|---|
| Formulation 1 | 10% Resveratrol/ATEC |
| Formulation 2 | 10% Resveratrol/(1:1 ATEC:EA) |
| Formulation 3 | 10% Resveratrol/5% PLGA 504H in ATEC |
| Formulation 4 | 10% Resveratrol/(1:1 Vitamin E acetate:Miglyol ® 810N) |

Miglyol® neutral oils are clear, slightly yellow esters of saturated coconut and palmkernal oil-derived caprylic and capric fatty acids and glycerin or propylene glycol (Miglyol® 840). More specifically, Miglyol® 810 and 812 neutral oils are caprylic/capric triglyceride; Miglyol® 818 is caprylic/capric/linoleic triglyceride (note that linoleic acid has antioxidant properties); Miglyol® 829 is caprylic/capric/succinic triglyceride; Miglyol® 840 is propylene glycol dicaprylate/dicaprate.

Figure 3:
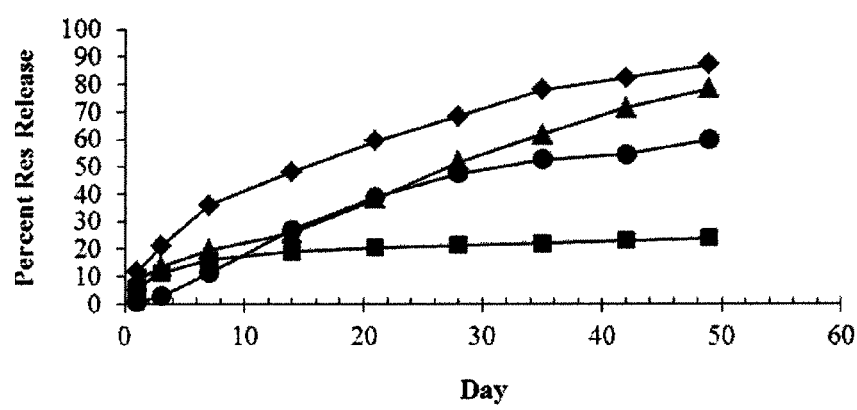
FIG. 3 is a graph reflecting in vitro release of a stilbenoid from four different sustained release formulations. Aliquots 25 µL; Ave (N=4). (♦) 10% Resveratrol/90% ATEC; (■) 10% Resveratrol/90% (1:1 ATEC:vitamin E acetate); (▲) 10% Resveratrol/90% (5% PLGA 504H in ATEC); (●) 10% Resveratrol/90% (1:1 Vitamin E acetate:Miglyol 810N from Sasol, Houston, Tex.).

For in vitro release study, aliquots of 25 µL (or 10 µL) of were placed in a 20 mL glass vial; then 10 ml of 0.9% saline was added, and the vial incubated at 37° C. At each time point, a 5 mL of sample was withdrawn from the vial, and its volume replaced with 5 mL of 0.9% saline to maintain infinite sink conditions. Resveratrol concentrations were determined using HPLC (Aliance, Waters Corp). The results are shown in FIG. 3.

Example 4

Combination Antioxidant Active Agent Formulations

Formulations consisting of more than one antioxidant, or antioxidant and steroid were made by mixing components as follows.

| | % Drug/Excipient |
|---|---|
| Formulation 1 | 20% timolol maleate:10% dexamethasone: 70% (1:1 ATEC:EA) |
| Formulation 2 | 10% timolol maleate:10% dexamethasone: 80% (1:1 ATEC:EA) |

Figure 6A:
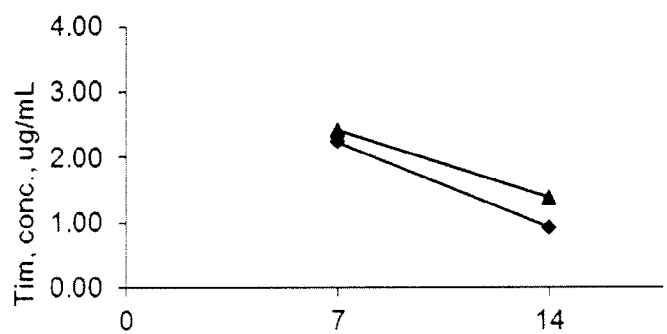
FIGS. 6A and 6B shows the concentrations (µg/mL) of timolol (tim) or dexamethasone (dex) in the eyes of rabbits 7 and 14 days after injection with a formulation of either 20% timolol maleate:10% dexamethasone:70% (1:1 ATEC:EA) (♦) or 10% timolol maleate:10% dexamethasone: 80% (1:1 ATEC:EA) (▲).
Figure 6B:
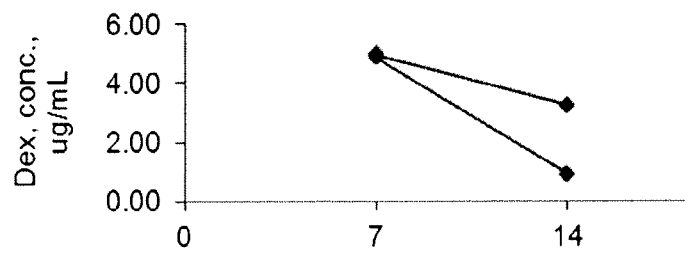
Figure 7A:
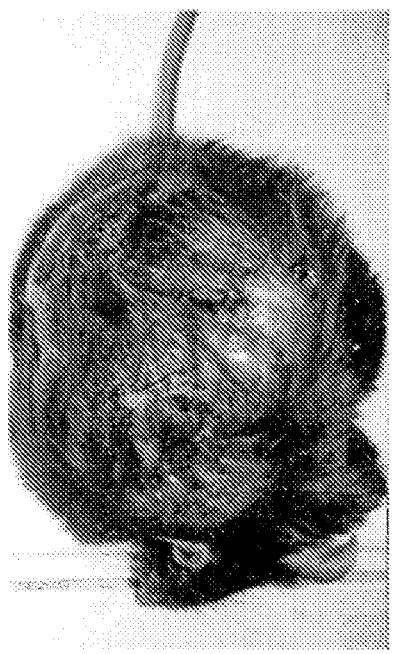
FIGS. 7A-7C present results of a single antioxidant intratumor administration in a mouse myeloma model of cancer. Photographs of an untreated B16 tumor in C57 mouse at 4 weeks (7A); and an astaxanthin:tocopherol acetate treated mouse at 2 weeks (7B).
Figure 7B:
Figure 7C:
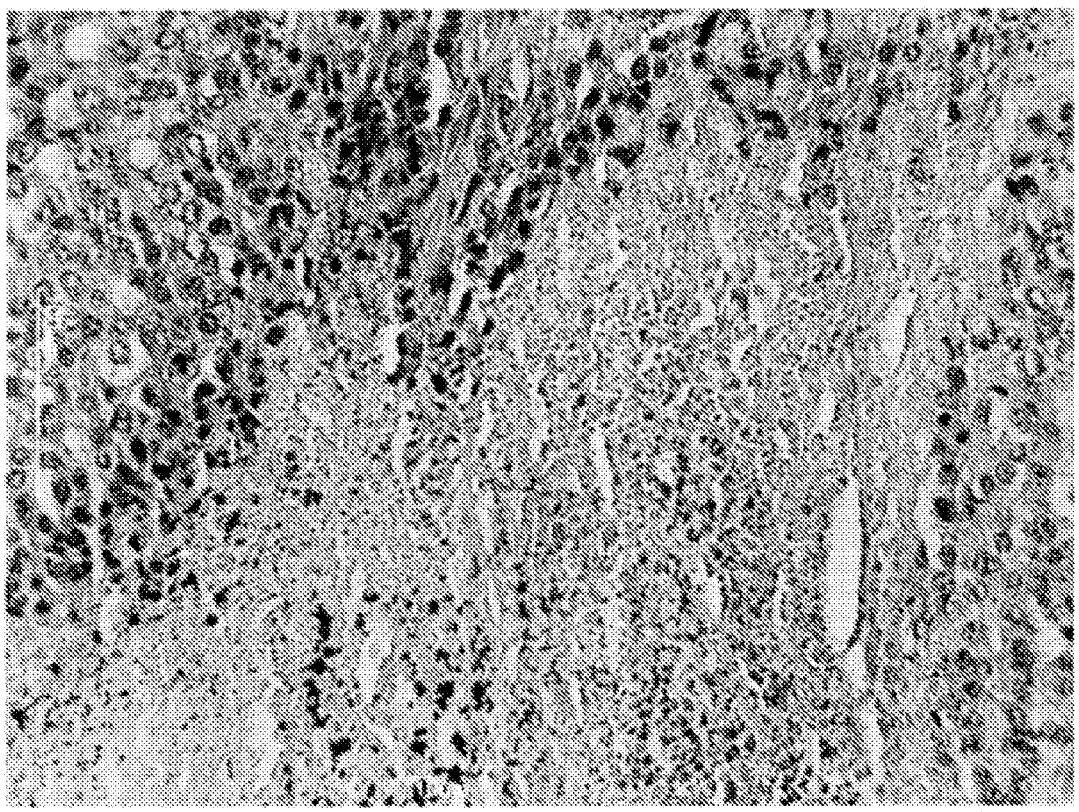

A 10 µL unit dose of either formulation 1 or formulation 2 was injected into the eyes of two rabbits, and the concentration of timolol or dexamethasone (dex) remaining in the eye tested at 7 days and 14 days thereafter. Results (average) are shown in FIGS. 6A and 6B. A 50 µL unit dose was injected into the vitreous of two rabbit's eyes, and the concentrations of active agent detected 7 days thereafter and averaged. Timalol was detected at 8.93 µg/mL; Dex was detected at 2.82 µg/mL.

A formulation consisting of 20% timolol maleate:10% Reservatrol:70% (1:1 ATEC:EA) was prepared by mixing. A unit dose of 50 µL was injected into the vitreous of two rabbit eyes, and Reservatrol was detected at 0.64 µg/mL (average) 7 days thereafter.

Example 5

Treatment of Tumors with Sustained Release Antioxidant Formulations

A mouse model was used to study the in vivo effect of sustained release antioxidant formulations on melanoma tumors. Mouse B16 melanoma Cell lines were obtained from NCI-Frederick, Md. C57 Mice were obtained from Simonsen Laboratories in Gilroy, Calif. Anesthesia was Ketamine/Xylazine/Acepromacine 1:1:0.03 mixture. C57 cell suspension and 1×1 mm tumor pieces were preserved in 90% Fetal Bovine Serum and 10% DMSO in liquid nitrogen. Tumor was also maintained by in vivo serial subcutaneous passage.

Mice of either sex, weighing 16-18 grams, were anesthetized with the ketamine mixture. Subcutaneous implantation of the B16 suspension (100 ul of $2 \times 10^6$/ml) or solid tumor piece were performed in the back or nape of the mouse. Tumors were treated when tumor reached the average size of 6×6 mm in diameter and weighed approximately 0.6-0.8 grams in 7-10 days.

Treatment consisted of a single intratumoral implantation of semi-solid drug formulations. Each formulation consisted of 2 mg of active pharmaceutical ingredient (API): either Resveratrol, Astaxanthin, or Melatonin; in either tocopherol acetate (EA), benzyl benzoate (BB), or acetyltriethyl citrate (ATEC) excipients (all Sigma Chemical). The ratio of API and excipient was 80:20 by weight.

Untreated animals lived on the average 3.5 to 4 weeks after implantation, at which time the tumor weighed approximately 30-40+ grams and measured greater than 1.75×1.75 cm.

In comparison, all the antioxidant treatment groups (i.e., all three antioxidants in all three excipients) showed definite antitumor activities in which one single administration of antioxidant exhibited anti-tumor efficacy. Changes observed with astaxanthin were most dramatic. The tumor stopped growing immediately after the single treatment, and peeling of the overlying skin surface and beginning ulceration appeared in about one week. Shrinkage of the tumor continued and was completely resolved clinically by 5-7 weeks. The animals remained active and continued to gain weight until termination of the experiment on day 90.

The following table compares the different formulations of astaxanthin (Ast) in sustained release excipient and their tumor effectiveness:

| Week | 0 | 1 | 2 | 3 | 4 | 5 | 6 | 7 |
|---|---|---|---|---|---|---|---|---|
| Ast/EA | +4 | +3.75 | +3 | +2 | +1 | 0 | 0 | 0 |
| Ast/BB | +4 | +4 | +3.5 | +3 | +2 | +1 | 0 | 0 |
| Ast/ATEC | +4 | +4 | +3.5 | +3.25 | +3 | +2 | +1 | 0 |

3 animals per group; Week 0 = treatment day. Average tumor size 6 × 6 mm +4 = tumor size 6 × 6 mm. 0 = resolution of tumor Modifications of the above described modes for carrying out the invention that are obvious to those of ordinary skill in the surgical, pharmaceutical, or related arts are intended to be within the scope of the appended claims.

We claim:

1. An antioxidant medicament for intratumoral injection or implantation for reducing the symptoms of cancer or inhibiting the growth of an established tumor, comprising 100 μmoles of each of the following five antioxidants: 6-O-palmitoyl-L-ascorbate, α-tocopheryl succinate, melatonin, resveratrol, and astaxanthin; wherein a unit dose of said medicament provides for sustained release of the antioxidant for at least 14 days.

2. The medicament of claim 1, wherein the sustained release medicament further comprises an additional active agent.

3. The medicament of claim 2, wherein the additional active agent is a steroid.

4. The medicament of claim 3, wherein the steroid is dexamethasone.

5. The medicament of claim 1, further comprising an excipient selected from the group consisting of tocopheryl acetate, tocopherol acetate, benzyl benzoate, a 1:1 mixture of acetyltriethyl citrate:tocopherol acetate, neutral oil comprising caprylic and capric fatty acids, or a combination of these.

6. The medicament of claim 5, further comprising no more than about 10% of a biodegradable, biocompatible polymer selected from the group consisting of poly(D,L-lactide), poly(D,L-lactide-co-glycolide), and a mixture of poly(D,L-lactide) and poly(D,L-lactide-co-glycolide).

\* \* \* \* \*